United States Patent [19]

Bocher

[11] 4,089,967
[45] May 16, 1978

[54] CREATININE PYRROLIDONE CARBOXYLATE, PHARMACEUTICAL COMPOSITIONS AND METHODS OF USE THEREOF

[76] Inventor: Dominique Bocher, 11, rue du Moulin Vert, 75014 Paris, France

[21] Appl. No.: 734,628

[22] Filed: Oct. 21, 1976

[30] Foreign Application Priority Data

Oct. 29, 1975 Luxembourg .......................... 73680

[51] Int. Cl.$^2$ .................. A61K 31/40; A61K 31/415; C07D 233/02
[52] U.S. Cl. .............................. 424/273 R; 424/274; 548/308
[58] Field of Search .............................. 424/273, 274; 260/309.7; 548/308

[56] References Cited

PUBLICATIONS

Chem. Abst. (1)-vol. 58-1317f (1963).
Chem. Abst. (2)-vol. 58-1314d (1963).
Chem. Abst. (3)-vol. 63-14642f (1965).

*Primary Examiner*—Stanley J. Friedman
*Attorney, Agent, or Firm*—Cushman, Darby & Cushman

[57] ABSTRACT

Creatinine pyrrolidone carboxylate which has the formula

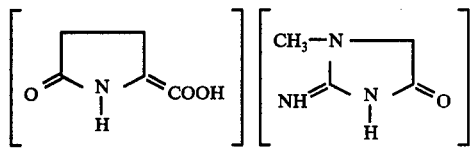

is prepared by heating at an elevated temperature creatinine base and pyrrolidone carboxylic acid in an aqueous solvent and concentrating the resulting reaction medium to dryness. This compound can be employed in a pharmaceutically acceptable excipient to treat asthenia of any origin, psychasthenia, neurosis and memory disorders.

9 Claims, No Drawings

CREATININE PYRROLIDONE CARBOXYLATE, PHARMACEUTICAL COMPOSITIONS AND METHODS OF USE THEREOF

The present invention relates to creatinine pyrrolidone carboxylate, to a process for preparing the same; to a pharmaceutical composition containing said creatinine pyrrolidone carboxylate and to the treatment of asthenia of any origin, psychasthenia, neurosis and memory disorders using said pharmaceutical compositions.

Creatinine pyrrolidone carboxylate or 2-pyrrolidone-5-carboxylate of 2'-imino-1'-methyl-4'-imidazolidinone has the empirical formula: $C_9H_{14}O_4N_4$. This compound which can be represented by the following structural formula:

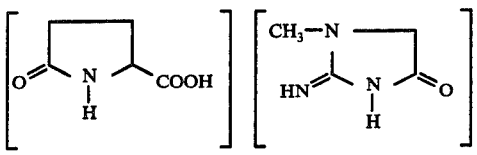

has a molecular weight of 242.21. Its elemental composition is as follows: C % = 44.62; H % = 5.82; O % = 26.41 and amorphous, cream yellow powder having a characteristic odor and a bitter taste. Its melting point is 155° C and a 10% aqueous solution thereof is a clear solution having a pH between about 3.5-4.

Creatinine pyrrolidone carboxylate is very soluble in water; only slightly soluble in alcohol; but insoluble in certain organic solvents such as acetone, benzene, chloroform and ether. Analytically this compound contains 53.3% pyrrolidone carboxylic acid and 46.7% creatinine.

The present invention also relates to a process for preparing creatinine pyrrolidone carboxylate which comprises reacting at an elevated temperature a mixture of pyrrolidone carboxylic acid and creatinine base, in an aqueous solvent for said mixture. Preferably, equimolar amounts of these reactants are employed.

The reaction is preferably carried out at the boil for a period of about 15 to 45 minutes. After the reaction, the reaction medium is permitted to cool and thereafter the cooled reaction mixture is filtered and then evaporated to dryness under a vacuum at a temperature of about 50° C. During this latter operation, the temperature is is progressively reduced relative to an increase in the concentration of the desired product.

The solid creatinine pyrrolidone carboxylate thus recovered is then powdered, and, if desired, recrystallized in water so as to provide the same in purified form.

The principal process of the present invention provides creatinine pyrrolidone carboxylate in a crude state with a very high yield. However, certain variations can be introduced into the process of the present invention without departing from the scope thereof.

The present invention also relates to creatinine pyrrolidone carboxylate as a medicine. In a preferred embodiment of this invention, the creatinine pyrrolidone carboxylate is admixed with a conventional pharmaceutically acceptable excipient.

Certain salts of pyrrolidone carboxylic acid have previously been proposed for use as a medicine in the treatment, particularly, of asthenia of any origin, of neurosis and of memory disorders; however, these salts, if they exhibit a very good activity, are not devoid of certain disadvantages which, consequently, render them difficultly useful in therapeutic treatments.

Creatinine pyrrlidone carboxylate essentially is completely devoid of the disadvantages of the above previously known salts of pyrrolidone carboxylic acid and is therefore particularly desirable and effective, taking into account principally its very weak toxicity, in the treatment of depressive states and memory disorders.

As indicated above, creatinine pyrrolidone carboxylate is a new molecule having its own physical and chemical properties as well as quite precise therapeutic characteristics.

The creatinine pyrrolidone carboxylate of the present invention is more particularly useful because of its refreshing and energy-producing action in human therapy as well as in animal therapy.

Pharmacologic studies made on laboratory animals have established the excellent properties of creatinine pyrrolidone carboxylate. These properties are essentially characterized by an excellent stimulating action on the nervous system, as well as by a resistive action to muscular fatigue.

Creatinine pyrrolidone carboxylate exhibits then a general tonic action. More particularly, due to its restorative properties, it possesses a rapid and durable anti-asthenia action; due to its energy-producing properties, it improves the resistance of the organism to fatigue, to attacks and to infections; due to its psycho-detoxicant properties, it improves the memory and the intellectual efficiency without provoking psychic excitation; and finally, due to its psycho-energetic properties, it provides psychic improvement, favors sleep, and favors physical and intellectual effort by acting on the cerebral metabolism.

Toxicologic studies involving male Swiss mice and Wistar rats have established that creatinine pyrrolidone carboxylate is practically devoid of toxicity.

I - Acute toxicity test on mice.

(1) Orally (probang): creatinine pyrrolidone carboxylate is administered to the said mice at a rate of 6000 mg/kg in a 60% solution in distilled water. Seven days after this treatment, no toxic phenomenon and no mortality occur.

(2) Intraperitoneally: Creatinine pyrrolidone carboxylate is administered at a rate of 3000 mg/kg, in a 30% solution in distilled water. Seven days after the administration, no mortality was registered.

II - Acute toxicity tests on rats.

Intraperitoneally: 3000 mg/kg and 5000 mg/kg, respectively, in a 30% and 50% solution in distilled water were administered to the Wistar rats. Seven days after the treatment, there was registered for the 3000 mg/kg treatment, 0% mortality, and for 5000 mg/kg treatment, a 40% mortality.

III - Subacute toxicity test in mice.

There were administered to mice for 5 consecutive days:

(1) orally (probang) - 2000 mg/kg of creatinine pyrrolidone carboxylate in solution having a volume of 0.2 ml/20 g.

Seven days after the treatment, no mortality was registered and no state of excitation was noted.

(2) intravenously - 650 mg/kg of creatinine pyrrolidone carboxylate, administered at a rate of 0.4 ml/20 g did not provoke the death of any animal during this treatment.

The acute and subacute toxicity tests have also established the absence of major secondary effects in the central domain.

The pharmaceutical compositions of the present invention contain generally from 0.05 to 80 percent by weight of creatinine pyrrolidone carboxylate. These compositions can be present under various forms. For example, they can be provided in liquid form with the active compound being in solution in an alimentary liquid such as an aromatized aqueous solution. They can also be provided in solid form, such as in the form of granules, pills, tablets, lozenges or gelatin capsules. They can also be provided in an injectable form.

The excipients usually employed to produce the solid ingestible compositions of the present invention are those conventionally used for these types of compositions. Representative excipients are described in U.S. Pat. No. 2,888,380.

The present invention also relates to a process of treating asthenia of any origin, neurosis and memory disorder. This treatment comprises administering, preferably orally, a pharmaceutical composition containing creatinine pyrrolidone carboxylate and appropriate pharmaceutically acceptable excipients.

The duration of the treatment can vary, but generally it lasts between one and three to four weeks, and the treatment involves the administration of said creatinine pyrrolidone carboxylate at a daily dosage rate in the order of 0.250 g to 5 g, but preferably from 0.5 to 2 g.

According to a preferred embodiment of this process, the administration of the daily dosage is carried out in two portions at meal time, for example, one in the morning and the other at mid-day.

Further, in the pharmaceutical compositions of the present invention, the creatinine pyrrolidone carboxylate can be employed alone or in combination with other therapeutic agents.

The activity of creatinine pyrrolidone carboxylate has also been demonstrated by significant clinical testing on humans.

This clinical study has established the excellent therapeutic activity of creatinine pyrrolidone carboxylate in the case of physical and psychic asthenia, post-operative convalescence, academic slowness, and intellectual over exertion.

The following representative results have been observed:

(1) A 48 year-old male convalescing from a particularly severe viral infection was extremely lethargic, had a short attention span and suffered from memory failure. He was submitted to a treatment of creatinine pyrrolidone carboxylate at a rate of 0.250 g thereof twice a day, which amounted to a daily dosage of 0.5 g which was administered in the form of a powder dissolved in fruit juice. At the end of five days, his lethargy was markedly decreased, his attention span was considerably improved so that he was able to read normally and his memory faculties were significantly improved.

(2) A 53 year-old male, suffering from depression brought about by his professional difficulties was in a state of prostration, was profoundly melancholy, exhibited misanthropic tendencies and suffered from insomnia.

This subject was then submitted to an 8-day treatment of creatinine pyrrolidone carboxylate administered to him at a rate of 1 gram per day in two 0.5 g doses, one in the morning and the other at noon.

After this treatment, the subject slowly regained his normal faculties and his insomnia had totally disappeared.

The following non-limiting examples illustrate the preparation of creatinine pyrrolidone carboxylate and several pharmaceutical compositions containing the same. Unless otherwise stated, all parts and percentages are by weight.

Preparation of creatinine pyrrolidone carboxylate.

1290 g (10 moles) of pyrrolidone carboxylic acid and 1131 g (10 moles) of base creatinine are added to 6.5 liters of purified water. The resulting admixture is then heated to a temperature of about 70° C so as to ensure completely dissolution of these two compounds to be reacted. The resulting solution is then brought to the boil for about ½ hour. Thereafter the reaction medium is left to cool slowly and then is filtered.

After filtration, the desired product is evaporated to dryness under a vacuum at a temperature of about 50° C. The temperature of this operation is progressively decreased in proportion to increases in the concentration of the product so as to avoid any degradation of the product.

The crude product thus obtained is then pulverized and optionally recrystallized in water so as to obtain creatinine pyrrolidone carboxylate in purified form.

In accordance with this process, 2300 g of creatinine pyrrolidone carboxylate, for a yield in the order of 95%, are obtained. The melting point of the crude product is about 150°–155° C and the melting point of the product after recrystallization is 154° to 155° C.

| Elemental Analysis | Calculated | Found |
| --- | --- | --- |
| C | 44.62% | 44.68% |
| H | 5.82% | 5.90% |
| N | 23.08% | 22.62% |
| O | 26.41% | 26.17% |

Examples of Pharmaceutical Compositions

EXAMPLE 1

A pharmaceutical composition in the form of a syrup is prepared by admixing the following components:

| | |
| --- | --- |
| Creatinine pyrrolidone -carboxylate | 15 g |
| Syrup | 70 ml |
| Raspberry fragrance | 4 ml |
| Distilled water, q.s.p. | 100 ml |

EXAMPLE 2

A pharmaceutical composition in the form of tablets is prepared by admixing the following components:

| | |
| --- | --- |
| Creatinine pyrrolidone carboxylate | 0.250 g |
| Perfume of honey | 0.025 g |
| Perfume of caramel | 0.075 g |
| White sugar, crystallized | 2.2 g |
| Tragacanth mucilage | 0.2 g |

EXAMPLE 3

A pharmaceutical composition in the form of 10 ml drinkable ampoules are prepared by admixing the following components:

| | |
|---|---|
| Creatinine pyrrolidone carboxylate | 0.250 g |
| Aromatized excipient, q.s.p. | 10 ml |

These can be provided, for instance, in a package containing twenty of these drinkable ampoules.

EXAMPLE 4

A pharmaceutical composition in the form of gelatin capsules are prepared by admixing the following components:

| | |
|---|---|
| Creatinine pyrrolidone carboxylate | 0.250 g |
| Gelatin excipient, sufficient to make the capsules | |

These can be provided, for instance, in a package containing 20 of these capsules.

What is claimed is:

1. Creatinine pyrrolidone carboxylate having the formula

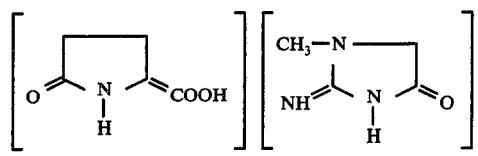

2. A pharmaceutical composition useful to treat asthenia, psychaesthenia, neurosis and memory disorders comprising in a pharmaceutically acceptable excipient creatinine pyrrolidone carboxylate present in an amount between 0.05 and 80 percent by weight thereof.

3. The composition of claim 2 wherein said excipient is an alimentary liquid.

4. The composition of claim 3 wherein said alimentary liquid is an aromatized aqueous solution.

5. The composition of claim 2 wherein said excipient is an ingestible solid.

6. The composition of claim 5 in the form of a lozenge, a gel, tablets or granules.

7. A process for treating asthenia, psychasthenia, neurosis and memory disorders comprising orally administering to a human creatinine pyrrolidone caboxylate in a pharmaceutically acceptable excipient, said creatinine pyrrolidone carboxylate being administered at a daily dosage rate between 0.250 and 5 g.

8. The process of claim 7 wherein said treatment lasts between 1 and 3-4 weeks.

9. The process of claim 7 wherein the daily dosage rate is between 0.5 to 2 g.